# United States Patent
Deck

(10) Patent No.: US 7,456,550 B2
(45) Date of Patent: Nov. 25, 2008

(54) DRIVE UNIT FOR MEDICAL DEVICES

(75) Inventor: Frank Deck, Niederkirchen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/832,458

(22) Filed: Aug. 1, 2007

(65) Prior Publication Data

US 2008/0007141 A1 Jan. 10, 2008

Related U.S. Application Data

(63) Continuation of application No. PCT/EP2006/050529, filed on Jan. 30, 2006.

(30) Foreign Application Priority Data

Feb. 1, 2005 (DE) ........................ 10 2005 004 498

(51) Int. Cl.
*H01L 41/08* (2006.01)
(52) U.S. Cl. ..................................................... 310/328
(58) Field of Classification Search ................. 310/328, 310/323.02
See application file for complete search history.

(56) References Cited

U.S. PATENT DOCUMENTS

| 4,383,195 | A  |   | 5/1983  | Kohn |
| 4,935,659 | A  | * | 6/1990  | Naka et al. ................... 310/328 |
| 5,726,520 | A  | * | 3/1998  | Grahn ........................ 310/328 |
| 6,313,566 | B1 |   | 11/2001 | Cunningham |
| 7,119,478 | B1 | * | 10/2006 | Mentesana ................... 310/328 |
| 7,166,953 | B2 | * | 1/2007  | Heim et al. .................. 310/333 |
| 2004/0127819 | A1 |  | 7/2004  | Roe |
| 2006/0049720 | A1 | * | 3/2006 | Henderson et al. .......... 310/328 |

FOREIGN PATENT DOCUMENTS

DE       10 2004 037 270       3/2006

\* cited by examiner

*Primary Examiner*—Mark Budd
(74) *Attorney, Agent, or Firm*—Bose McKinney & Evans LLP

(57) ABSTRACT

The invention relates to a drive unit for a medical device such as an insulin pump, lancing device, or test strip magazine. The drive unit comprises an actuator for charging a mechanical energy storage element. The actuator oscillates and executes travel strokes which are transmitted by means of a step-up element to a nonreturn rotor or traveler for prestressing the mechanical energy storage element and driving a movement element.

56 Claims, 11 Drawing Sheets

DRIVE UNIT FOR MEDICAL DEVICES

RELATED APPLICATIONS

This is a continuation application of International Application PCT/EP2006/050529, filed Jan. 30, 2006, which claims priority to DE 10 2005 004 498.0, filed Feb. 1, 2005, which are hereby incorporated by reference in their entirety.

BACKGROUND

The present invention relates to a drive unit, in particular a drive unit which is suitable for portable medical devices and with the aid of which movements to be carried out slowly can be automated.

In portable medical devices, e.g., glucose measuring devices, the automatic lancing of a body part and the subsequent automatic recovery of blood from the puncture site formed as a result of the lancing operation play an essential role. To convert electrical energy from a long-term electrical storage element specific to the glucose measuring devices, e.g., accumulators or batteries, into mechanical energy, electric motors or electromagnets are used, according to the prior art. With the aid of these drive units, either a pricking movement is executed directly or a secondary mechanical energy storage element, e.g., in the form of a spring, is charged and is subsequently highly dynamically discharged in order to generate the pricking movement (cf. DE 10 2004 037 270.5). In particular, the charging of a spring element which may be used as a secondary mechanical energy store or storage element requires a drive unit which is capable of applying the spring force or the spring torque necessary for prestressing a torsion spring. In order to apply these high forces and torques, e.g., direct-current motors used as electric motors are equipped with high-reduction gears.

The electric motors used hitherto in glucose measuring systems must normally be equipped with a gear in order to increase the torque for prestressing a secondary mechanical energy storage element. However, these gears have poor efficiencies, particularly when high step-up ratios are used. Moreover, these gears produce running noises and take up a large construction volume which, in glucose measuring devices, is available to only a very limited extent for reasons of simple handling. Moreover, gears with high step-up are mostly provided with metal gearwheels and with exact mountings, thus making them very costly to produce. Consequently, gears with high step-up, used for prestressing secondary mechanical energy storage elements, undesirably on the one hand considerably enlarge the dimensions of an integrated glucose measuring system and on the other hand considerably increase its production costs.

U.S. Pat. No. 4,383,195 discloses a piezoelectrically actuated snap fastener. A piezoelectric actuator contains a piezoelectric element. A snap device is disclosed, by means of which a force can be generated which is directed in the opposite direction to the expansion generated by the piezoelectric element. This force is a predetermined reaction force having to be overcome in order to trigger a snap-in of the snap device. The piezoelectric element comprises piezoelectric means for providing a force which opposes the snap connection and which overshoots the reaction force, and also means for applying an electrical field to the piezoelectric means, so that the force acting in the opposite direction can be generated and energy can be stored in the snap device, thus making the snapping of the device possible.

U.S. Pat. No. 6,313,566 relates to a piezoelectrically actuated motor. The piezoelectric motor disclosed contains a motor body and a layer connected to the motor body. Several small legs are connected to this layer in such a way that the small legs are attached to a substrate. Each of the small legs contains a piezoelectric wafer. The actuation of a piezoelectrically active wafer displaces a corresponding small leg in relation to the substrate. This displacement generates a transmission of energy to the layer. The energy stored in this way in the layer can be utilized in such a way that the motor moves along the substrate. The small legs are capable of moving independently of one another and are likewise capable of moving sequentially or within predetermined groups or units. The small legs may also be arranged in pairs, the individual small legs of a pair of small legs executing a simultaneous movement. The motor makes it possible to maintain a high holding force when the energy supply is absent.

In light of the outlined disadvantages of the prior art, it would be desirable to provide a drive unit with small external dimensions and an actuator which generates high actuating forces and which may be arranged within a portable measuring device to fulfill a plurality of functions.

SUMMARY OF THE INVENTION

These teachings disclose a drive unit, e.g., for a measuring device or an insulin pump, which may comprise a pricking device for the recovery of body fluid and comprises an actuator which serves for charging a mechanical energy storage element. The actuator may be provided, e.g., as a piezoactuator, its length change when it is connected to a voltage source being transmitted by means of a transmission element to a nonreturn rotor for prestressing the mechanical energy storage element. By virtue of the transmission element, the stroke of the piezoactuator, which amounts to only a few micrometers, can be stepped up into a greater stroke which is transmitted to the nonreturn rotor. The rotor is in this case assigned a nonreturn means or element which, when the length change of the piezoactuator is canceled, prevents its return movement to its initial position and preserves the stroke travel covered during the preceding cycle of the piezoactuator. In the case of an oscillating voltage supply of the piezoactuator, the shortstroke piezoactuator movements are thus added to form a large overall stroke which acts on the nonreturn rotor.

The actuator of the drive unit may also be implemented in another embodiment using a diaphragm capable of being acted upon by a pressure medium. Advantageously, in this embodiment, a diaphragm material is used which deflects when a cavity is acted upon by pressure and which deforms due to deflection. This deformation which occurs when the cavity closed by the diaphragm material is acted upon by pressure can be transmitted to a step-up element which increases the stroke movement according to a defined step-up ratio. In this embodiment, the stroke achievable during the deformation cycle of the diaphragm material when the latter is deflected is dependent on the diaphragm material, on the material thickness of the diaphragm material and on the action of pressure upon the cavity closed by the diaphragm material. The cavity, which is closed by the diaphragm material according to this embodiment, may be acted upon by a pressure medium, e.g., a gas, or be acted upon by liquids, e.g., water or oil.

As a further embodiment of an actuator for a portable measuring device or for an insulin pump, the actuator may also be designed as a micromotor. The micromotor drives a cam of rounded form which has essentially an oval contour. During the rotation of an output shaft of the micromotor, the cam connected fixedly in terms of rotation to the output shaft is set in rotation and contacts a step-up element, capable of being formed, e.g., as a lever, once or several times per revolution, depending on the design variance of the cam. An oscillating movement of a step-up element can thereby be achieved, the latter transmitting a deflection of a lever end caused by the rotational movement of the cam into a nonreturn rotor in accordance with the step-up configuration of the step-up element.

In an advantageous embodiment, a piezoactuator may be connected to an oscillating voltage source and be recharged. What can be achieved via the oscillating voltage supply of the piezoactuator is that the stroke movements, taking place with high forces during the length change of the piezoactuator comprising a stack of piezocrystals, for the prestressing of, e.g., a rotor designed as a torsion or leaf spring, are transmitted without the need for a gear.

In particular, by a suitable choice of the step-up element between the nonreturn rotor and the piezoactuator, the step-up element can transmit length changes of the piezoactuator to the nonreturn rotor in a ratio of, e.g., 1:25 and above. Consequently, a greater stroke can be transmitted to the non-return rotor per charging/discharging cycle of the piezoactuator, as compared to the stroke movement which the piezocrystal stack of the piezoactuator executes according to its length change when a voltage is applied.

Due to the nonreturn means advantageously assigned to the nonreturn rotor, when the piezoactuator is discharged the stroke of the nonreturn rotor covered during the previous length change can be preserved on the latter. The nonreturn means may be designed either as a ratchet wheel or as an external deformation, e.g., a kind of external toothing or teeth, on the rotor guided in a guide. The nonreturn means is preferably dimensioned such that its lost motion is kept lower than the executed travel of the transmission element at its long end. The nonreturn means assigned to the nonreturn rotor has a lost motion which is lower than the stroke achievable, e.g., via a piezoactuator. This ensures that the actuator stroke at the prolonged end of the step-up element is also actually transmitted to the nonreturn rotor and actually advances the rotor during a charging/discharging cycle of the piezoactuator. The lost motion of the nonreturn means, comprising, e.g., a detent pawl, which couples with teeth on the nonreturn rotor, corresponds to the amount of tooth spacing of the teeth on the nonreturn rotor.

In the transmission element embodiment, the latter is designed as a pivoting lever which is rotatable about a pivot axis within a medical device for the recovery of body fluids. To implement a step-up ratio, the pivoting lever comprises a first and a second lever arm end which are produced in a different length, depending on the desired step-up ratio. The step-up element, which may be designed in the form of a pivoting lever, couples the stroke movement of the piezocrystal stack of the piezoactuator. The movement of the nonreturn rotor, whether a ratchet wheel or a rotor of block-shaped design which is guided in a guide, has a positive or nonpositive nonreturn.

In a first embodiment according to the invention, an oscillatingly activated piezostack actuator with a lever and rotor is used. The lever mechanism implements a step-up of the piezoactuator stroke, which is typically between 3 μm and 20 μm, into a greater stroke of a few tenths of mm, e.g., between 0.3 and 0.5 mm. This greater stroke is transferred to the nonreturn rotor. The prevention of the return movement of the rotor during the contraction of the piezoactuator in the course of its discharging phase takes place by a nonreturn means, e.g., a pawl detent. Owing to the repetitions of charging/discharging cycles of the piezoactuator, the short-stroke actuator movements are added to form a large overall stroke.

According to this principle, mechanical energy can be stored in the mechanical energy storage element charged by the nonreturn rotor. This mechanical energy storage element may be, e.g., a linear or torsion spring. In a similar way, by the rotor being prestressed continuously by means of the piezoactuator, the movement of parts of a medical device, e.g., of a test strip or of a test strip drum, or the drive of an insulin pump can be implemented.

The step-up element used, e.g., a rotatably mounted lever provided with different lever arms, can be produced by plastic injection molding or by metal stamping. The nonreturn rotor, e.g., a ratchet wheel or a rotor of block-like design guided in guides, and the bearings may likewise be manufactured by plastic injection molding. Consequently, the entire drive unit can be produced cost-effectively, requiring a small amount of construction volume and which produces extremely low noise. Moreover, high levels of efficiency can be achieved by dispensing with a gear comprising a plurality of gearwheels, this being extremely important for the energy balance in medical devices for the recovery of body fluids or in insulin pumps.

In a further embodiment according to the invention, the piezoactuator capable of being used within a medical device, e.g., an insulin pump, is activated by means of an alternating voltage of the desired operating frequency. The medical device may be, as well as an insulin pump, a measuring device or analyzer with individual test strips or with a multiplicity of test strips received in a magazine. Furthermore, the disclosed drive unit may be employed in integrated systems with a pricking aid and with an evaluation unit for sample evaluation. In these devices, by means of the disclosed drive unit, system functions, such as the triggering of the pricking operation, the transport and feed of the test strip or the transport of the test strip magazine can be achieved. Also, the disclosed drive unit may be used in straightforward blood sampling devices. The longer the piezocrystal stack of the piezoactuator used is, the greater the working stroke is which can be achieved. The stroke brought about by the length change of the piezocrystal stack (typically 1.5 μm length change per 1 mm of crystal stack length) is transmitted to the coupled, rotatably mounted step-up element. Owing to the step-up ratio set by virtue of the design of the step-up element, the stroke of the lever tip, which acts, e.g., on a nonreturn rotor designed as a ratchet wheel, is increased. During the expansion of the piezoactuator, the ratchet wheel rotates, a nonreturn means enabling this direction of rotation by means of a spring-loaded rotational movement. During the contraction of the piezoactuator in the course of the discharge phase, the step-up element designed as a lever is reset into its initial position by spring force. In this case, the nonreturn means, which comprises a detent pawl and the ratchet wheel, prevents the rotation of the ratchet wheel opposite to the direction of rotation, with the result that a secondary energy storage element can be prestressed.

The nonreturn means, which, according to this embodiment, may comprise a ratchet wheel and a detent pawl assigned to the latter, can alternatively also be designed as a clamping body freewheel, as a wrap spring freewheel or as a frictional locking mechanism.

In a another embodiment, a linearly operating arrangement of a drive unit for a medical device, e.g., an insulin pump, can be made available. According to this embodiment, the piezostack actuator cooperates with a step-up element of lever-shaped design and a spring. According to this embodiment, the nonreturn rotor is provided with a nonreturn means which is of fishbone-like form. One side of the rotor of block-shaped design, guided in a guide, cooperates with the guide surrounding the rotor of block-shaped design, in such a way that the inclined individual ribs on an outer face of the rotor are inclined with respect to the prestressing movement of the rotor of block-shaped design. As a result, a forward movement of the rotor of block-shaped design becomes possible for the prestressing of a secondary energy storage element, the reverse movement of which, however, is inhibited, during the discharge phase of the piezoactuator, due to the ribs which come to bear against the linear guide.

In a further embodiment of the drive unit for a medical device, e.g., for the recovery of body fluids, or an insulin pump, the piezoactuator can be assigned a rocker-shaped lever of a design bent in a U-shaped manner. The lever, serving as a step-up element and supported on a bearing, comprises a long and a short leg. The rocker-shaped lever is supported on an abutment of the housing. The piezoactuator stroke transmitted by the step-up element is converted radially into a rotational movement. According to this embodiment, a shaft has two clamping roller freewheels, one of the outer rings of one of the clamping roller freewheels being connected firmly to the shaft. An outer ring of the other freewheel is connected stationarily to the device housing of the medical device, e.g., for the recovery of body fluids, or of an insulin pump. A spring, formed on the device side, for a pricking aid for making a body fluid sampling orifice can be connected to the end of the shaft and be prestressed as a result of the rotational movement of the latter. After the triggering of, e.g., a pricking aid, the spring expanded at the same time can be rotated anew unidirectionally in one direction (i.e., a 360° drive).

In a further embodiment, the drive unit is designed as an axially operating drive unit. According to this embodiment, the piezocrystal stack actuates a drive bell via a lever pincer having a solid joint. The drive bell is mounted rotatably on an output shaft. A rotational movement of the drive bell generated during the charging phase of the piezoactuator is transmitted to a freewheel star provided inside the drive bell. The freewheel star is, in turn, rotationally fixedly attached to the output shaft. During the contraction of the piezoactuator in the course of the discharge phase, a torsion spring rotates the drive bell back into its initial position; during this resetting movement, the freewheel star surrounded by the drive bell and consequently the output shaft cannot co-rotate back within a freewheel bell. Due to the successive charging and discharging cycles of the piezoactuator, this gives rise on the output shaft to a unidirectional rotational movement which runs in one direction and which may be utilized for storing energy in a mechanical energy storage element. According to this axially operating embodiment, the nonreturn means comprises the freewheel star, the drive bell and the freewheel bell. Alternatively, in this embodiment, a clamping body freewheel, a wrap spring freewheel or else a frictional locking mechanism may also be employed.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Medical devices are understood below to mean those devices which recover a body fluid, e.g., blood, by pricking the skin by means of automatic lancing and taking blood from the extraction point thus made and deliver it to a test strip. The medical devices described in more detail below comprise either one or several test strips which are received in a magazine or a drum. When a medical device of this type is in operation, it is provided with a voltage source, whether it be a battery or an accumulator, via which actuators serving as drives can be supplied with a voltage. The voltage sources constitute long-term electrical stores or storage elements, the electrical energy of which is converted into mechanical energy. The mechanical energy serves for triggering pricking movements and/or for prestressing a secondary mechanical energy storage element, with the aid of which a pricking movement taking place highly dynamically can be brought about. Furthermore, the disclosed drive unit can be employed as a drive unit for an insulin pump or for the transport of test strips or of a magazine, e.g., a drum magazine, receiving a multiplicity of test strips.

Figure 1:
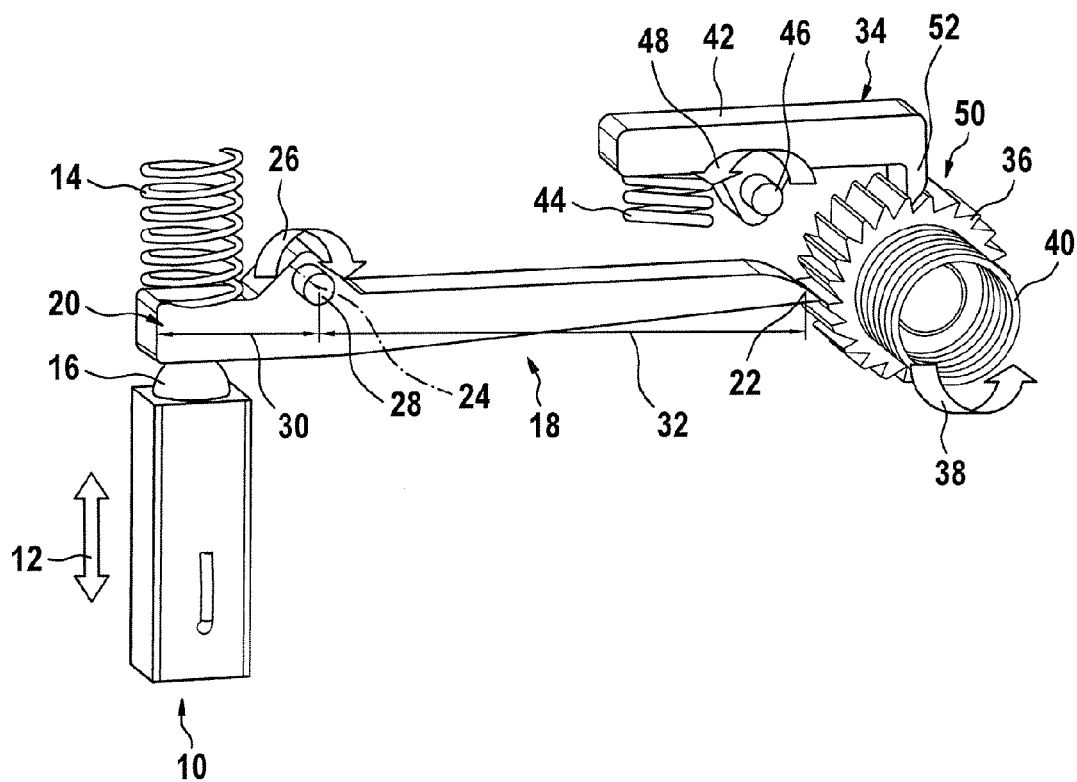
FIG. 1 is a perspective view of a first embodiment of a drive unit having a nonreturn means and a piezoactuator.

FIG. 1 shows a first embodiment of a drive unit provided with a piezoactuator and a nonreturn means or element. Piezoactuator 10 comprises a multiplicity of piezocrystals which are arranged one above the other in a stack. During the charging phase of the piezoactuator 10, a length change of each individual piezocrystal takes place, which, added up, leads to a length change in the piezocrystal stack of the order of between 3 μm and 20 μm. In the illustration according to FIG. 1, the length change of the piezoactuator 10 is designated by the double arrow 12. When a voltage is applied during the charging phase of the piezoactuator 10, a length change takes place in the latter. The piezocrystal stack of the piezoactuator 10 contracts to its original length during the discharging phase of the piezoactuator 10.

The piezoactuator 10 illustrated in FIG. 1 is assigned an actuator head 16 which acts upon a first end 20 of a step-up element 18 of lever-shaped design. The actuator head 16 acts, e.g., upon a first lever arm 30 of the step-up element 18, while a restoring element 14 provided as a spring is provided above the first lever arm 30 of the step-up element 18. The step-up element 18 having a lever-shaped design comprises first end 20 already mentioned and second end 22. The step-up element 18 is mounted pivotably or, rotatably about an axis of rotation 24. When a voltage is applied to the piezoactuator 10, the step-up element 18 executes a movement in a direction of rotation 26. The axis of rotation 24 of the step-up element 18 is received, fixedly with respect to the housing, in a bearing 28. Furthermore, the step-up element 18 of lever-shaped design comprises a second lever arm 32, the second end 22 of which couples to a nonreturn rotor provided as a ratchet wheel 36. As illustrated in FIG. 1, the ratchet wheel 36 comprises, e.g., teeth 50. The second end 22 of the step-up element 18 engages into the interspaces between the teeth 50.

A nonreturn means or element 34 is arranged above the ratchet wheel 36. The nonreturn means 34 includes a detent pawl 42 and is movable about a rotary bearing 46. The detent pawl 42 is itself acted upon by a restoring element 44. On the underside of the detent pawl 42 is located a hook 52 which projects into the free spaces of the teeth 50 on the circumference of the nonreturn rotor designed as a ratchet wheel 36.

During the charging phase of the piezoactuator 10, the latter executes a length change 12. As a result, the actuator head 16 moves the first lever arm 30 of the step-up element 18 upward against the action of the restoring element 14. The step-up element 18 is thereby pivoted in the direction of rotation 26 about the axis of rotation 24. The second end 22 formed on the second lever arm 32 of the step-up element 18 engages into the interspaces of the teeth 50 which are formed on the circumference of the ratchet wheel 36, and rotates the ratchet wheel 36 in the direction of rotation 38. A secondary mechanical energy storage element 40, illustrated as a torsion spring, is thereby prestressed. During the rotation of the ratchet wheel 36 in a second direction of rotation 38, the hook 52 formed on the underside of the detent pawl 42 travels, due to the geometry of the teeth 50 with a steep flank and a gradually rising flank, from free space to free space on ratchet wheel 36 of the integrated measuring device. The secondary energy storage element 40 is prestressed by virtue of the rotational movement of the ratchet wheel 36.

The nonreturn means 34, comprising the detent pawl 42 which cooperates or couples with the external side of teeth 50 of ratchet wheel 36, has with respect to the tooth spacing of the teeth 50 and to the hook-shaped projection 52 a lost motion which is dimensioned smaller than, e.g., a tooth spacing of the external side of the teeth 50 of the ratchet wheel 36 via which the secondary mechanical energy storage element 40 is prestressed. This ensures that, when voltage is applied to a piezoactuator 10, its stroke travel also actually translates into an advancing movement, that is to say, in this case, into a rotational movement ratchet wheel 36. If teeth are provided on the ratchet wheel 36, the lost motion of the nonreturn means 34 is lower than the tooth spacing of the teeth on the circumference of the ratchet wheel 36.

When the charging phase of the piezoactuator 10 is completed, the length change 12 of the piezocrystal stack which has occurred decreases during the discharging phase of the piezoactuator 10, and the piezoactuator 10 resumes its original length. The step-up element 18 is reset about the axis of rotation 24 by the restoring element 14 assigned to the first lever arm 30. In order to prevent the ratchet wheel 36 from likewise executing a resetting movement during the discharging phase of the piezoactuator 10, the hook 52 on the underside of the spring-loaded detent pawl 42 blocks the return rotation of the ratchet wheel 36 opposite the direction of rotation 38. The nonreturn means 34, that is to say the arrangement consisting of the nonreturn rotor designed as a ratchet wheel 36 and having external teeth 50 and detent pawl 42, encounters lost motion which is less than the executed lever travel during the charging phase of the piezoactuator 10. Due to the design of the first lever arm 30 and of the second lever arm 32 in terms of the step-up ratio, for each charging/discharging cycle of the piezoactuator 10 the stroke of the latter can be increased, in the event of a length change 12 from 3 μm to 20 μm, to a stroke travel at the second end 22 of the second lever arm 32 of a few tenths of mm, e.g., of between 0.2 mm and 0.5 mm. Since the mechanical energy content of the secondary mechanical energy storage element 40 recovered during the charging phase of the piezoactuator 10 during the preceding charging phase of the piezoactuator 10 remains stored in the secondary energy storage element 40 because the return rotation of the ratchet wheel 36 is prevented, during a subsequent charging/discharging cycle of the piezoactuator 10 a further rotation of the ratchet wheel 36 in the direction of rotation 38 can be achieved, so that, in the case of oscillating repetitions of the length change 12 on the piezoactuator 10, a large overall stroke or a high overall rotation can be achieved on the rotor, and a continuous prestressing of, e.g., the secondary mechanical energy storage element 40 provided as, e.g., a spring, is achieved.

When the secondary mechanical energy storage element 40 is prestressed, it can be discharged highly dynamically, which may be utilized, e.g., for carrying out a pricking movement of a lancet in a blood sampling device. This lancet, e.g., pricks the human skin, so that an outlet orifice for a body fluid, e.g., blood, is obtained. In addition to the highly dynamic discharging of the secondary mechanical energy storage element 40, which may be in the form of a torsion spring, a helical spring or a linear spring, the movement of a test strip, of a drum receiving a plurality of test strips or of a differently configured test strip magazine in integrated medical devices, which are preferably designed to be portable, can be implemented via the energy content stored in the secondary mechanical energy storage element 40. Furthermore, an insulin pump may be provided with a drive unit of this type.

The transmission element 18, which is of lever-shaped design in the embodiment illustrated in FIG. 1, can be produced in a way which lowers the production costs, e.g., as a plastic injection-molded or as a metal stamping component. The nonreturn means 34 with a nonreturn rotor designed as a ratchet wheel 36 and having external teeth 50 can also be manufactured as a plastic injection-molded component. Thus, the drive unit for converting electrical energy of the long-term storage element into mechanical energy to be reserved in a secondary energy storage element 40 can be accommodated cost-effectively, in particular so as to take up little construction volume, in the housing of a medical device. The drive unit is distinguished, in particular, by production of very little noise, very high efficiency being achievable since a wheel mechanism is avoided. This, in turn, is conducive to the service life of the long-term energy storage element, e.g., an accumulator or a battery, received in the medical device, e.g., an insulin pump.

Figure 2A:
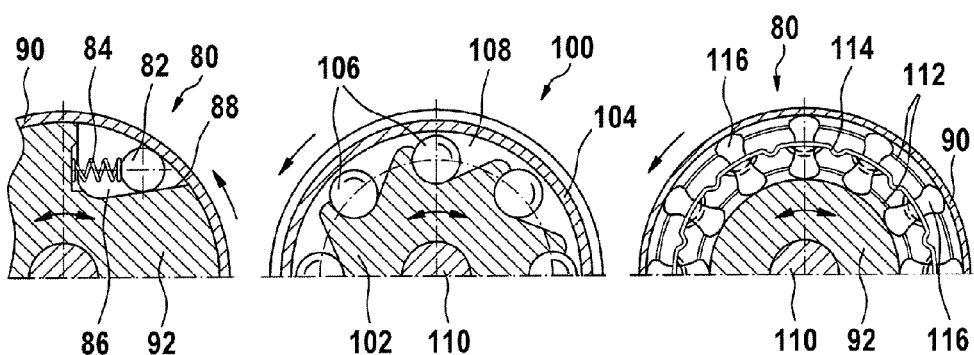
FIG. 2a is a series of schematic views of embodiments of the nonreturn means with a clamping body freewheel.
Figure 2B:
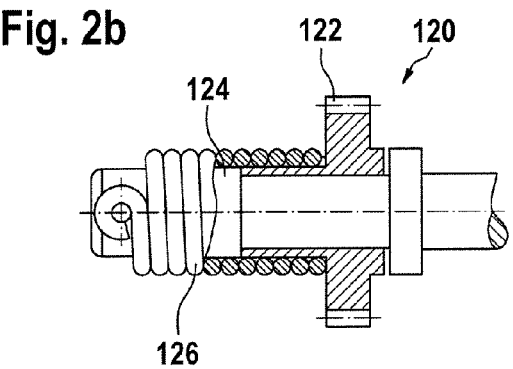
FIG. 2b is a perspective view in partial cross section of an embodiment of the nonreturn means with a wrap spring freewheel.
Figure 2C:
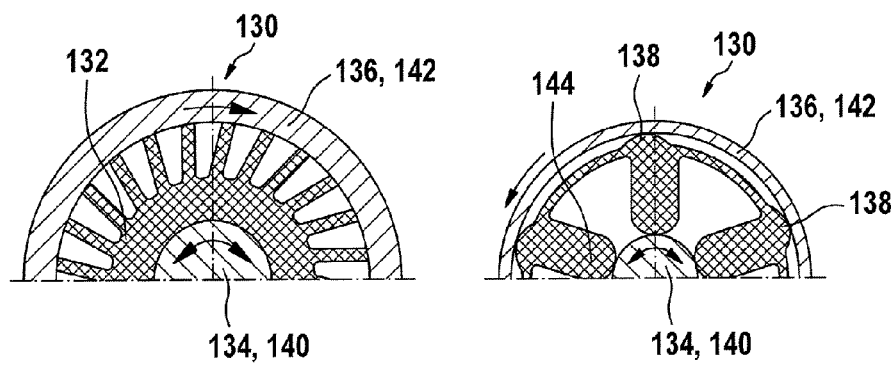
FIG. 2c is a series of schematic views of embodiments of the nonreturn means with a frictional locking mechanism.

Variations of nonreturn means which can be used within the framework of these teachings may be gathered from the sequence of FIGS. 2a, 2b and 2c.

Instead of the nonreturn means 34 illustrated in the embodiment according to FIG. 1, the nonreturn means 34 may also be designed as a clamping roller freewheel 80. The clamping roller freewheel 80 illustrated in FIG. 2a comprises a plurality of clamping rollers 82. The clamping rollers 82 are acted upon via a spring 84 and received in recesses 86 of a shaft 92. Each of the recesses 86 comprises a slope 88, the spring 84 which acts in each case upon the clamping roller 82 being supported on a side of the recess 86 which is oriented approximately perpendicularly with respect to the slope 88. The recess 86 is surrounded by a tubular surface 90. During the clockwise movement of the tubular surface 90, the spring-loaded clamping rollers 82 are placed between the inner face of the tubular surface 90 and the slope 88, so that the shaft 92 in which the recesses 86 are provided is also moved clockwise. If, by contrast, the surface 90 of tubular design is moved counterclockwise, the tubular surface 90 rotates freely relative to the shaft 92, in which the recesses 86 are formed, freely, a take-up effect being absent. Accordingly, only during the rotation of the clamping body freewheel 80 clockwise, the clamping rollers 82 are clamped between the tubular surface 90 and the shaft 92, in which the recesses 86 are formed, and thus give rise to the take-up effect.

A clamping roller freewheel with an inner star is designated by reference symbol 100. Clamping bodies 106 of roller-shaped or spherical design are provided in recesses 108 on the inner star 102. As soon as the clamping bodies 106 run onto the obliquely formed portions on the bottom of the respective recesses 108, the clamping bodies 106 come to bear against the inner face of the tubular body 104 and take up the latter counterclockwise according to the arrow depicted in the middle of FIG. 2a. Via the clamping roller freewheel 100, illustrated in the middle of FIG. 2a, with an inner star 102, either a freewheel or a clamping connection can be achieved, depending on whether the tubular body 104 or the shaft 110 is driven.

Furthermore, a further clamping body freewheel 80 may be gathered from the illustration according to FIG. 2a, comprising an expanding band spring 114 in which a plurality of drivers 116 are received, spaced apart from one another, as seen in the circumferential direction. Depending on the direction of rotation of the shaft 110, the drivers 116 fixed by the expanding band spring 114 come to bear against the underside of the tubular surface 90 and thus bring about a clamping connection between shafts 92, 110 and the tubular surface 90. The individual drivers 116, which are spaced apart from one another, as seen in the circumferential direction, are held in double cages 112. A freewheel or a clamping connection between the shafts 92, 110 and a tubular body 90 can also be implemented by means of the clamping body freewheel 80 formed on the right in FIG. 2a. Whether there is a clamping connection or freewheel depends on whether the tubular surface 90 or the shaft 92, 110 is driven. This affords degrees of freedom as regards to the design of the clamping body freewheel 80 in terms of the output side and the drive side.

A wrap spring freewheel which would be used in the integrated measuring device may be gathered from the illustration according to FIG. 2b.

The wrap spring freewheel 120 illustrated in FIG. 2b comprises a spring 126 which is wrapped around a sleeve-shaped extension of a gearwheel. The drive side of the gearwheel is identified by reference symbol 122 and the output side by reference symbol 124. The spring 126 arranged on the sleeve-shaped extension of the drive-side gearwheel 122 has a plurality of turns which surround the sleeve-shaped extension on the drive-side gearwheel 122. Depending on the direction in which the gearwheel 122 is driven on the drive side, the spring 126 is wrapped to a higher or lower degree around the sleeve-shaped tenon and thus drives the shaft received by the gearwheel arranged on the drive side 122 or allows this shaft to run freely.

Embodiment of frictional locking mechanisms may be gathered from the illustration according to FIG. 2c. The embodiment, illustrated in the illustration according to FIG. 1, of the nonreturn means 34 may also be implemented by the frictional locking mechanism illustrated in FIG. 2c. In the frictional locking mechanisms 130 illustrated in FIG. 2c, in each case either a clamping ring 132 of comb-shaped design or a clamping body ring 144 provided with cams is illustrated. The comb-shaped clamping ring 132 has a plurality of ribs arranged at an inclination which bear against the inner face of a roller 136 forming an output side 142. Depending on the direction in which the comb-shaped clamping ring 132 received fixedly in terms of rotation on a shaft 134 forming the drive side 140 rotates, the ribs of said clamping ring which project in a comb-shaped manner come to bear against the inner face of the roller 136. When the shaft 134 is operated clockwise, the roller 136 is taken up. If a rotation of the shaft 134 counterclockwise takes place, the ribs of comb-shaped design on the circumferential surface of the comb-shaped clamping ring 132 slip past the inner circumferential surface of the roller 136.

Furthermore, a frictional locking mechanism 130 which contains a clamping body ring 144 may be gathered from the illustration according to FIG. 2c. The clamping body ring 144 comprises individual projections 138 which project in a raised manner and which bear against the inner circumferential surface of a roller 136. The roller 136 forms the output side of the frictional locking mechanism 130. The frictional locking mechanism 130 is driven from the drive side 140 via the shaft 134. When the shaft 134 is driven clockwise, the raised projections 138 are moved away from the inner circumferential surface of the roller 136 due to the offset between the raised projections 138 and the cams of the clamping body ring 144. When the shaft 134 is operated counterclockwise on the drive side 140, the raised projections 138 provided on the outer circumferential surface of the clamping body ring 144 come to bear against the inner face of the roller 136 and take up the latter counterclockwise.

Figure 3:
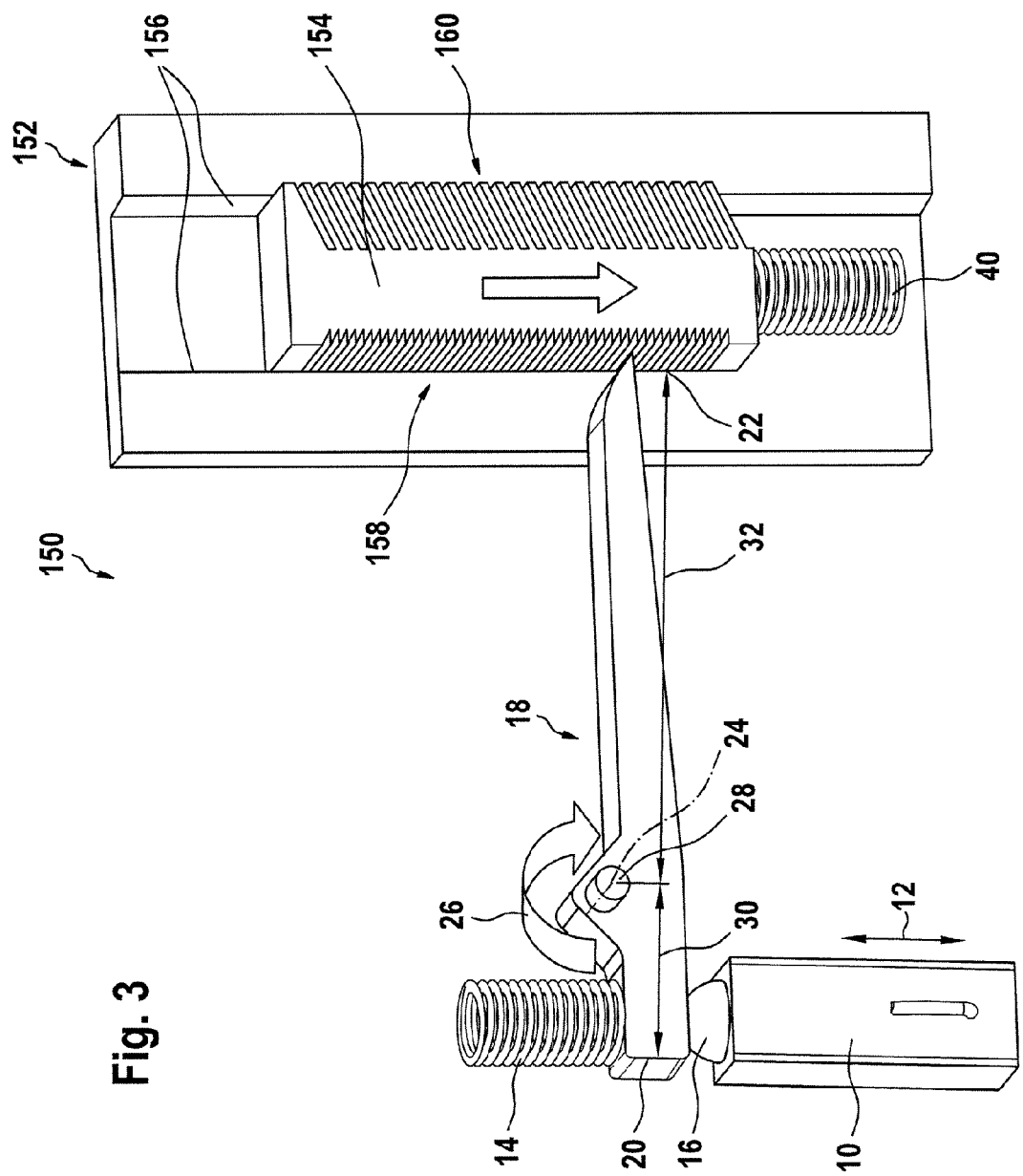
FIG. 3 is a perspective view of an embodiment of a drive unit with a step-up ratio.

A further embodiment of the drive unit for a medical device, e.g., an insulin pump, may be gathered from the illustration according to FIG. 3. In a similar way to the illustration according to FIG. 1, a piezoactuator 10 is provided which executes a length change 12 during a charging phase. When voltage is applied to the piezoactuator 10, its actuator head 16 moves onto the underside of the step-up element 18 and deflects the step-up element 18 of lever-shaped design about its axis of rotation 24 in the direction of rotation 26. In this case, the restoring element 14 is compressed. The step-up element 18 of lever-shaped design, illustrated in the embodiment according to FIG. 3, also comprises a first lever arm 30 and a second lever arm 32, by means of the length dimension of which the step-up ratio of the step-up element 18 can be set. While the first end 20 of the step-up element 18 is moved upward about the axis of rotation 24 during the pivoting movement of the step-up element 18, the second end 22 of the second lever arm 32 moves downward with respect to the axis of rotation 24. The tapering end of the second end 22 of the second lever arm 32 engages into teeth on a first traveler side 158 of a nonreturn traveler 154 of block-shaped design. The nonreturn traveler 154 of block-shaped design is movable linearly and is received in a guide 156. A nonreturn means 152 is given by the formation of a second traveler side 160 of the linearly movable traveler 154 of block-shaped design. During a downward movement which is imparted to the nonreturn traveler 154 of block-shaped design during the deflection of the step-up element 18 about the axis of rotation 24, the traveler 154 of block-shaped design moves downward in a vertical direction according to the arrow and compresses the secondary energy storage element 40 which is provided as a helical spring in the embodiment shown in FIG. 3. By virtue of the configuration of the second traveler side 160 with a rib structure of comb-shaped design with inclined ribs, the downward movement of the traveler 154 of block-shaped design in the vertical direction downward is not impeded. When the nonreturn traveler 154 of block-shaped design is deflected downward in the guide 156, the rib structure of comb-shaped design on the second traveler side 160 prevents the block-shaped nonreturn traveler 154 from moving back in its guide 156. This is brought about by the respective ends of the ribs on the second traveler side 160 being brought to bear against the smooth inner face of the guide 156. The nonreturn traveler 154 of block-shaped design therefore remains in its position during the discharging phase of the piezoactuator 10 until, at the next charging phase of the piezoactuator 10, the second end 22 of the step-up element 18 of lever-shaped design is moved downward anew and moves the traveler 154 of block-shaped design further downward in its guide 156 as a result of engagement on the teeth on the first traveler side 158.

Consequently, the oscillating stroke movement of the piezoactuator 10 is stepped up into a continuously added-up stroke movement of the nonreturn traveler 154 of block-shaped design. Depending on what lever lengths the first lever arm 30 or the second lever arm 32 has with respect to the axis of rotation 24 of the transmission element 18, a step-up of the length change 12 of the piezoactuator 10 into a correspondingly greater stroke travel of the traveler 154 of block-shaped design can be achieved. The piezoactuator 10 is activated by means of an alternating voltage of the desired operating frequency. The longer the piezoactuator 10 used is designed to be, that is say the more piezocrystals are layered one above the other, the higher the length change 12 which can be achieved when voltage is applied to the piezoactuator 10. The length change of a piezocrystal stack normally amounts to 1.5 µm per 1 mm of piezocrystal stack length.

The secondary energy storage element 40 acted upon by the nonreturn traveler 154 of block-shaped design may be designed as a torsion spring, as a helical spring or as a linear spring. The secondary energy storage element 40 may both be coupled to the nonreturn traveler 154 of block-shaped design and constitute a separate component decoupled from this. By means of the embodiment, illustrated in FIG. 3, of the drive unit for converting electrical energy into mechanical energy within a medical device, a secondary mechanical energy storage element 40 for the highly dynamic triggering of a lancing movement can be prestressed, test strip transport within the medical device can be carried out or an advancing movement of a test strip reservoir of drum-shaped or magazine-shaped design within a medical device can be implemented. In addition, by means of the drive unit, an insulin pump in which extremely small stroke movements are required over a long operating period can be achieved.

Figure 4:
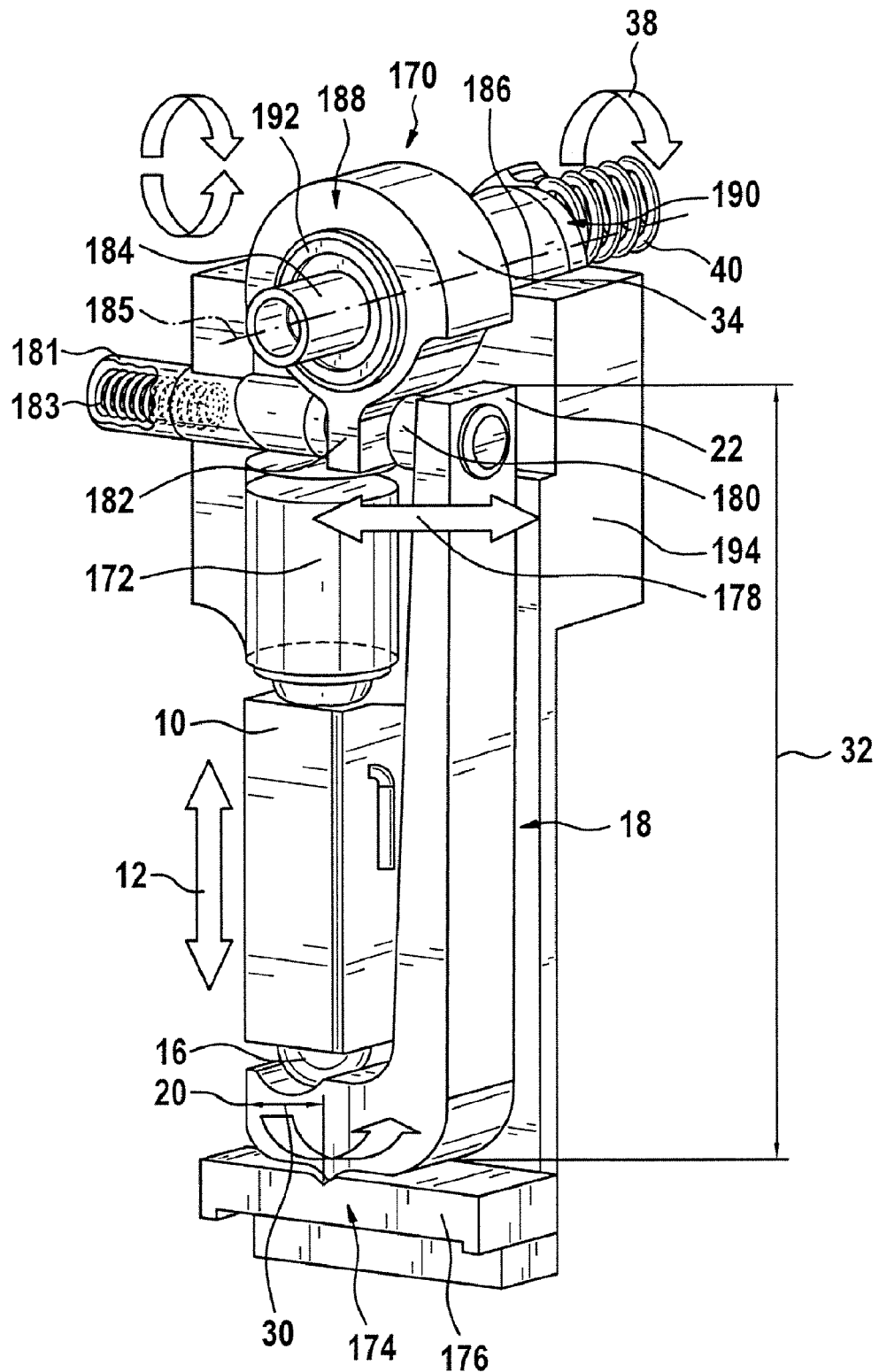
FIG. 4 is a perspective view of a piezoactuator integrated into a pricking drive for tensioning a drive spring.

A drive unit for tensioning a secondary mechanical energy storage element for a pricking drive may be gathered from the illustration according to FIG. 4. It may be gathered from the illustration according to FIG. 4 that the piezoactuator 10 is built into the medical device and is supported on the housing side against an abutment. The length change 12 of the piezocrystal stack of the piezoactuator 10 is transmitted to the actuator head 16. The actuator head 16 rests in a cup-shaped recess of the first end 20 of a step-up element 18. According to the embodiment illustrated in FIG. 4, the step-up element 18 is of angled design and comprises the first end 20 of the first lever arm 30 and the second end 22 on the second lever arm 32. The step-up element 18 rests in a pivot bearing 174 against an abutment 176 provided fixedly with respect to the housing. During a length change 12 for the piezoactuator 10, a downward deflection of the first lever arm 30 takes place, thus leading to a lateral pivoting movement of the second lever arm 32 according to the double arrow 178 depicted. A pedestal 180 arranged at the second end 22 of the second lever arm 32 acts on a cam 182 of a pricking drive 170. The stroke stepped up by the step-up element 18 during a length change 12 of the piezoactuator 10 is transferred via the pedestal 180 at the second end 22 of the second lever arm 32 to the cam 182. The cam 182 is connected fixedly to the outer ring of a first clamping roller freewheel 188. An outer ring of a second clamping roller freewheel 190 is connected stationarily to the device housing 194 of the medical device. A secondary mechanical energy storage element 40, provided on the device side, for the pricking drive 170 is coupled to one end of the rotatable shaft 184 and is prestressed during the deflection of the cam 182. The rotatably received shaft 184 is mounted in a shaft bearing 186 in the device housing 194 which is reproduced only partially in the illustration according to FIG. 4. While the first clamping roller freewheel 188 is connected on its outer ring to the cam 182 at a fixed location, the outer ring of the second clamping roller freewheel 190 is connected stationarily to the device housing 194.

In the illustration according to FIG. 4, reference symbol 181 designates a pressure piece with a spherical head. The pressure piece 181 with a spherical head is arranged opposite the pedestal 180 which is received at the second end 22 of the step-up element 18 of lever-shaped design. Inside the pressure piece 181 with a spherical head is located a spring 183 which acts with spring force upon the spherical head of the pressure piece 181. Reference symbol 185 designates the bisecting line of the shaft 184 received in the clamping roller freewheels 188 and 190. When the cam 182 is deflected during the charging phase of the piezoactuator 10 via the step-up element 18 of lever-shaped design, the spherical head, acted upon by the spring element 183, of the pressure piece 181 is prestressed counter to the action of the spring element 183. The return of the cam 182 into its initial position takes place by means of the spring 183 which is present in the pressure piece 181 with a spherical head and which resets the cam 182 into its initial position again during the discharging phase of the piezoactuator 10. The stroke movement of the step-up element 18 is thereby transmitted to the secondary mechanical energy storage element 40 received at one end of the rotatable shaft 184.

Figure 5:
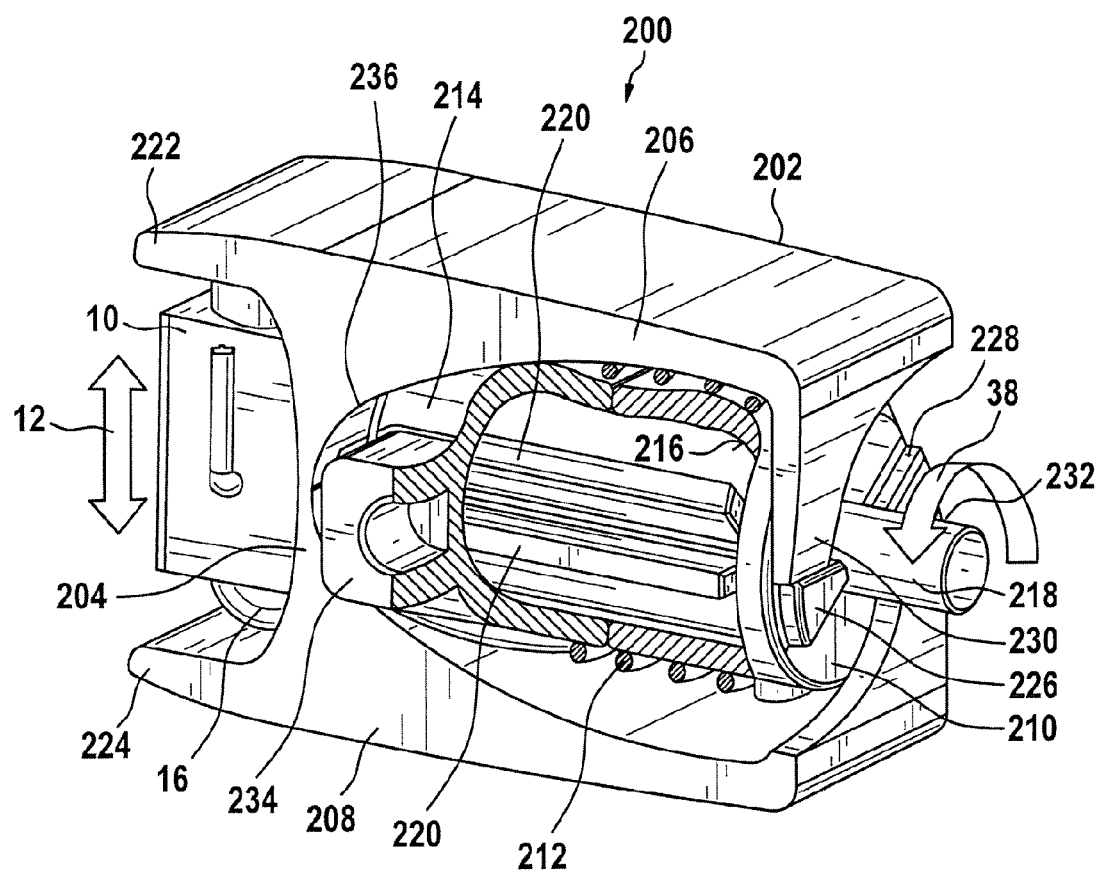
FIG. 5 is a perspective view of an embodiment of the drive unit in an axial embodiment with a small construction volume with portions cut away and shown in partial cross section.

Another embodiment of a drive unit according to these teachings, which is distinguished by an extremely low construction, volume and an axial type of construction may be gathered from the illustration according to FIG. 5. As shown in FIG. 5, the piezoactuator 10 is built into a medical device in an axial type of construction 200. A lever pincer 202 is provided, which has a solid joint 204, that is to say a point of weakened cross section. The lever pincer 202 comprises a first pincer leg 206 and a second pincer leg 208. In the event of a length change 12, the piezoactuator 10 acts in each case upon a first short leg 222 and upon a second short leg 224 of the lever pincer 202. During the charging phase of the piezoactuator 10, that is to say during its length change 12, a drive bell 210 is actuated.

The drive bell 210 is rotatably mounted on an output shaft 218. The drive bell 210 comprises on one end face cams 226, 228 which are acted upon in each case by extensions 230, 232 formed on the end faces of the pincer legs 206, 208. By the extensions 230, 232 being moved toward one another, the drive bell 210 is set in rotation according to the arrow given the reference symbol 38. The rotational movement of the drive bell 210 thus generated is transmitted to a freewheel 220 designed as an inner star. The freewheel 220 designed as an inner star is received fixedly in terms of rotation on the output shaft 218. The drive bell 210 is surrounded by a torsion spring 212. The ribs formed on the freewheel 220 designed as an inner star bear against an inner circumferential surface 216 of the drive bell 210. A freewheel bell 214 is provided coaxially to the drive bell 210 as a separate component from the drive bell 210. The freewheel bell 214 comprises an anti-twist device 234 of tenon-shaped design which lies in a recess 236 between the first pincer leg 206 and the second pincer leg 208.

During the contraction of the piezoactuator 10, the drive bell 210 is reset into its initial position again by the torsion spring 212. A backward rotation of the output shaft 218 is ensured by the freewheel bell 214 and the freewheel 220 which prevents a return rotation of the output shaft 218 opposite to the direction of rotation 38. During the discharging phase of the piezoactuator 10, the rotational movement of the output shaft 218 in the direction of rotation 38, caused by the rotation of the drive bell 210 during the previous application of voltage to said piezoactuator, is maintained, since a backward rotation of the output shaft 218 opposite to the direction of rotation 38 prevents a return rotation of the output shaft 218 by means of the ribs of the freewheel system 220 which bear against the inner circumferential surface of the freewheel bell 214. By contrast, a rotation of the freewheel 220 in relation to the freewheel bell 214 can take place in the direction of rotation 38 when a rotational movement is imparted to the drive bell 210.

Figure 6:
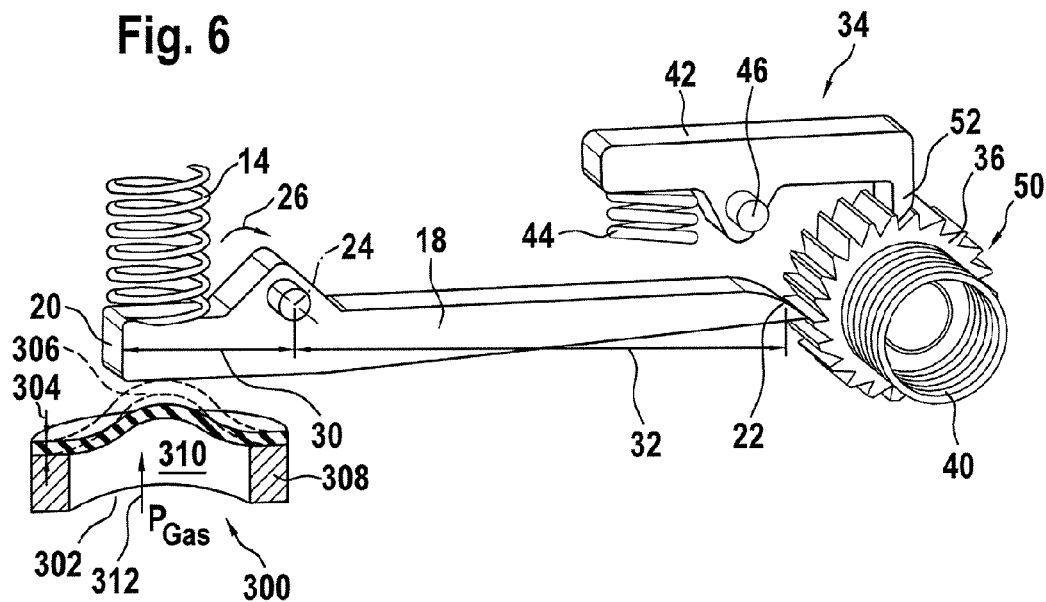
FIG. 6 is a perspective view in partial cross section of an embodiment of the drive unit with a deflectable diaphragm.

A further embodiment of the drive unit for a medical device or an insulin pump or the like is shown in FIG. 6. FIG. 6 illustrates an actuator 300 with a diaphragm. The actuator 300 is formed by a diaphragm which closes a cavity 302 capable of being acted upon by a pressure medium. The thickness of the diaphragm material is identified by reference symbol 304. The cavity 302 delimited by a wall 308 is acted upon by a gaseous medium, e.g., air, or by a liquid, e.g., water or oil. According to the action of pressure upon the cavity 302, a deflection 306 of the diaphragm takes place—reproduced in FIG. 6 in the deflected diaphragm position indicated by dashes. The cavity capable of being acted upon by a pressure medium 310 is closed sealingly by the diaphragm material. The actuator 300 with a diaphragm acts in the direction 312 on the lever-shaped step-up element 18 which can be used in this embodiment. The step-up element 18 of lever-shaped design can be actuated in the direction of rotation 26 about an axis of rotation 24. The step-up element 18 comprises a first end 20 at the end of a first lever arm 30 and a second end 22 at the end of the second lever arm 32. The first lever arm 30 is acted upon by a restoring element 14 designed in spring form. During the deflection 306 of the actuator 300 with a diaphragm, the diaphragm material contacts the underside of the first lever arm 30 of the step-up element 18 of lever-shaped design and deflects the step-up element 18 in the direction of rotation 26 about the axis of rotation 24.

The second end 22 of the step-up element 18, said second end engaging into teeth 50 on the circumference of the nonreturn rotor 36, here illustrated as a ratchet wheel, moves the nonreturn rotor 36 about its axis according to the illustration in FIG. 6 and consequently prestresses the secondary mechanical energy storage element 40 connected fixedly in terms of rotation to the nonreturn rotor. A return rotation of the nonreturn rotor 36 is avoided by means of the nonreturn means 34. In the embodiment according to FIG. 6, the nonreturn means 34 is designed as a detent pawl 42 which is arranged pivotably about the rotary bearing 46. One end of the detent pawl 42 is acted upon by a prestressing element 44, while the other end of the detent pawl 42 has formed on it a hook 52 which engages into the interspaces of the teeth 50 on the outer circumference of the nonreturn rotor 36—designed here as a ratchet wheel.

In this embodiment of the drive unit, the lost motion of the nonreturn means 34, of the detent pawl 42 and of the external teeth 50, is also dimensioned smaller than the stroke of the step-up element 18 of lever-shaped design at the second end 22 at which the latter engages into the teeth 50 of the nonreturn rotor 36. This ensures that, during a stroke of the actuator 300 with a diaphragm, a rotational movement of the nonreturn rotor 36 by the amount of at least one tooth spacing is actually achieved. In the illustration according to FIG. 6, the actuator 300 with a diaphragm is illustrated in an embodiment of low profile. The deflection 306, achievable by means of the actuator 300 with a diaphragm, for rotating the step-up element 18 of lever-shaped design is dependent on the selected diaphragm material and on the pressure to which the pressure medium 310 is exposed within the cavity 302. Depending on the degree of deflection 306 of the diaphragm material, a lower or higher deflection of the first lever arm 30 about the axis of rotation 24 of the step-up element 18 and, consequently, a smaller or larger stroke at the second end 22 of the second lever arm 32 of the step-up element 18 can be achieved.

Figure 7:
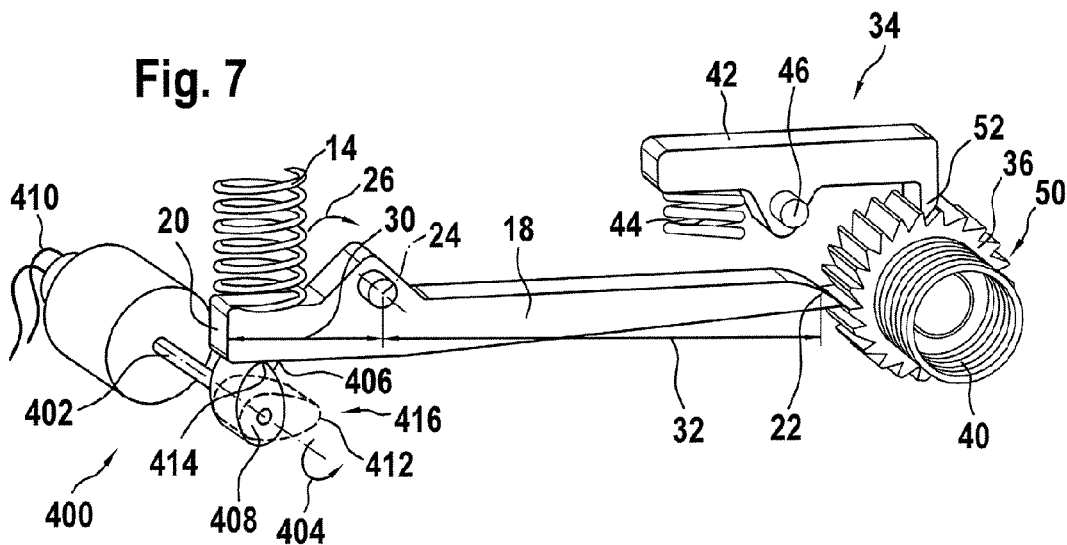
FIG. 7 is a perspective view of a further embodiment of the drive unit for portable measuring devices or insulin pumps, with a micromotor.

A further embodiment of the drive unit in which a micromotor is used, may be gathered from the illustration according to FIG. 7. It may be gathered from the illustration according to FIG. 7 that an actuator 400 with a micromotor is arranged at one end of the step-up element 18 of lever-shaped design. The actuator 400 with a micromotor comprises an output shaft 402 which is driven in the direction of rotation 404. Located at the end of the output shaft 402 is a cam 408 which has a contour 416 of oval design in the illustration according to FIG. 7. The cam 408 illustrated in the illustration according to FIG. 7 touches a contact surface 406 on the underside of the first lever arm 30 of the step-up element 18 of lever-shaped design once per revolution. For this purpose, the cam 408 has a contact point 414. In that position of the cam 408 which is illustrated by unbroken lines, the contact point 414 touches the contact surface 406 the first lever arm 30 and deflects the step-up element 18 of lever-shaped design about the axis of rotation 24 in the direction of rotation 26 counter to the action of the restoring element 14.

Instead of the cam 408 illustrated in FIG. 7 and provided on the output shaft 402 of the actuator 400 with a micromotor, a cam could also be used which touches the contact surface 406 of the first lever arm 30 at least twice or even more often per revolution.

According to the rotation of the actuator 400 with a micromotor, an oscillating deflection of the first lever arm 30 of the step-up element 18 of lever-shaped design, and consequently, a deflection of the second end 22 of the second lever arm 32 of the step-up element 18 of lever-shaped design takes place. As a result, the nonreturn rotor, designed as a ratchet wheel in the embodiment according to FIG. 7, has imparted to it a rotational movement which it transmits to the secondary mechanical energy storage element 40. During the return of the step-up element 18 of lever-shaped design, that is to say in the event that the contact point 414 of the cam 408 just avoids touching the contact surface 406 during a revolution of the cam 408, a return rotation of the nonreturn rotor 36 is prevented by the nonreturn means 34.

In the embodiment illustrated in FIG. 7, the nonreturn means 34 is similar to the nonreturn means of the embodiment according to FIG. 6. The lost motion of the nonreturn means 34 is in this case dimensioned such that it is lower than the stroke of the second end 22 on the second lever arm 32 of the step-up element 18 of lever-shaped design. This ensures that, during a deflection of the first lever arm 30 about the axis of rotation 24 of the step-up element 18, a rotation of the nonreturn rotor 36 provided with teeth 50 and designed as a ratchet wheel can be achieved.

Thus, the stroke movement at the second end 22 of the step-up element 18, previously achieved during a deflection of the step-up element 18 at the first end 20 of the first lever arm 30, leads to a rotational movement of the nonreturn rotor 36 counterclockwise, the return rotational movement of the nonreturn rotor 36 being prevented by the nonreturn means 34. In this way, an energy content can be stored in the secondary mechanical energy storage element 40 according to the working strokes of the step-up element 18 and can be utilized for triggering functions in a medical device, e.g., an insulin pump.

Figure 8:
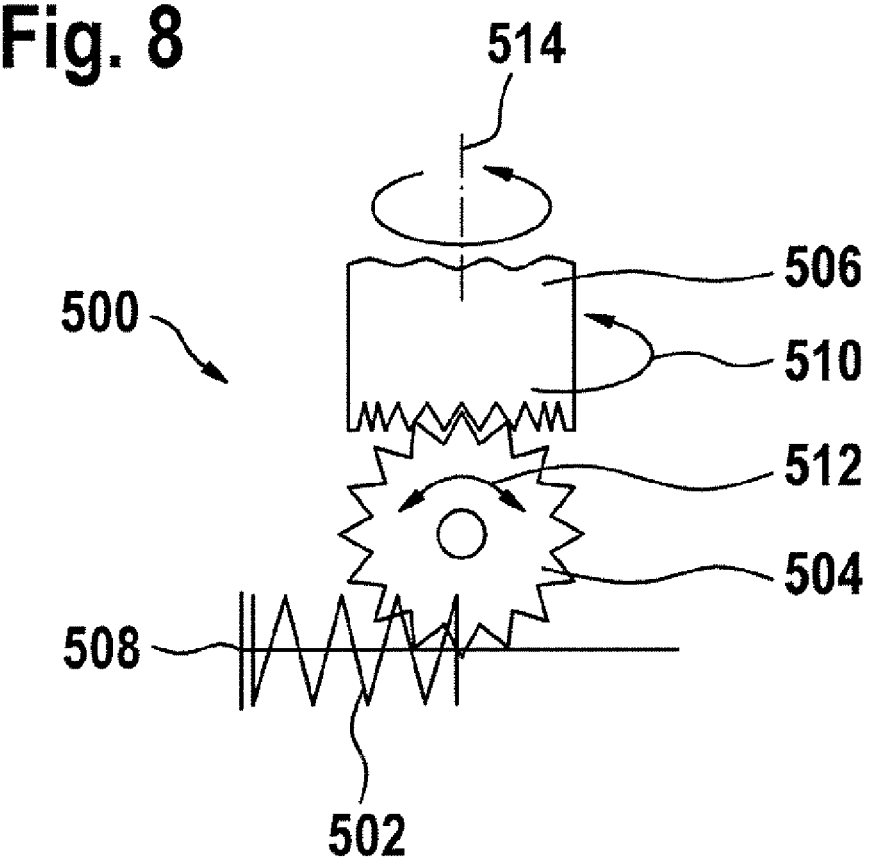
FIG. 8 is a schematic view of a combination drive unit.

FIG. 8 shows an illustration of a combination drive unit for a medical device. The combination drive unit 500 illustrated in FIG. 8 comprises a secondary mechanical energy storage element 502 which is reproduced only diagrammatically in the illustration according to FIG. 8. A gearwheel 504 is mounted rotatably in the combination drive unit 500 and can be rotated in both directions of rotation according to the double arrow 512. The gearwheel 504 is coupled both to the secondary mechanical energy storage element 502 for storing mechanical energy and directly to a housing side of a drum magazine 506. When the gearwheel 504 is driven by an embodiment of the above-described piezoactuator 10, a rotation of the gearwheel 504 takes place, with the result that the secondary mechanical energy storage element 502 is compressed. On the other hand, the gearwheel 504 engages into a correspondingly configured bottom of the drum magazine 506, so that the drum magazine 506 is rotated about its axis of rotation 514. The magazine may be provided for, e.g., the storage of test strips or lancets, so that a rotation of the drum magazine 506 takes place in such a way that a disposable in the drum magazine 506 is positioned correspondingly to an extraction unit in the medical device. Thus, it is conceivable that, e.g., during the tensioning of the secondary mechanical energy storage element 502 for driving a lancet, an advance of the drum magazine 506 about its axis of rotation 514 occurs simultaneously, so that a test strip can be extracted from the drum magazine 506 for sampling by means of an extraction unit provided for this purpose, e.g., by means of a plunger. The direction of rotation of the drum magazine 506 about the axis of rotation 514 is illustrated by the arrow 514.

Figure 9:
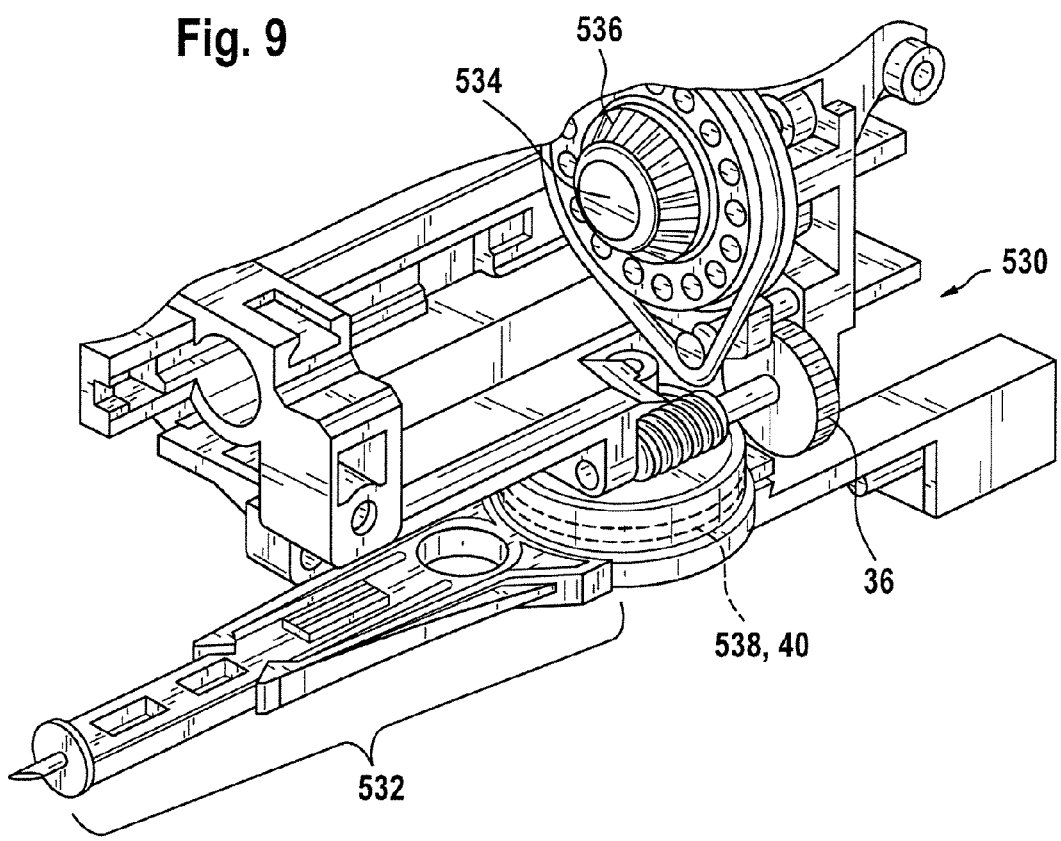
FIG. 9 is a partial perspective view of a system comprising a blood sampling system and a magazine transport with portions cut away.

FIG. 9 shows a partial illustration of an integrated system comprising a blood sampling system and a magazine transport. It may be gathered from the illustration according to FIG. 9 that an integrated system 530 comprises a pricking aid 532 and a drum magazine 506, not illustrated, but which may be gathered diagrammatically from FIG. 8. The drum magazine not illustrated in FIG. 9 is driven by means of a shaft 534. The shaft 534 comprises, at its end facing the drum magazine, a toothed structure 536 which functions as a driver for the drum magazine not illustrated in FIG. 9. The pricking aid 532 is accommodated in the lower region of the integrated system 530 according to the illustration in FIG. 9. An advance of the shaft 534 and the associated rotational movement of the drum magazine 506 according to FIG. 8 can be achieved by means of a drive unit, as described above. For this purpose, the shaft 534 may be coupled, e.g., to the output shaft 218 according to the illustration in FIG. 5. The piezoactuator 200, illustrated there, in an axial form of construction can, in addition to the shaft 534, also actuate the spiral spring 538 prestressing the pricking aid 532. The secondary mechanical energy storage element can be designed both as a helical spring 40 and as a spiral spring 538 indicated diagrammatically in FIG. 9. Furthermore, the nonreturn rotor, which can be designed as a ratchet wheel 36, may be gathered from FIG. 9, on which the piezoactuator 200 according to FIG. 5 acts. Of course, it is possible, in the integrated system 530 shown in FIG. 9, to also employ the embodiments of the drive unit according to FIGS. 1, 4 and 6 and 7.

Figure 10:
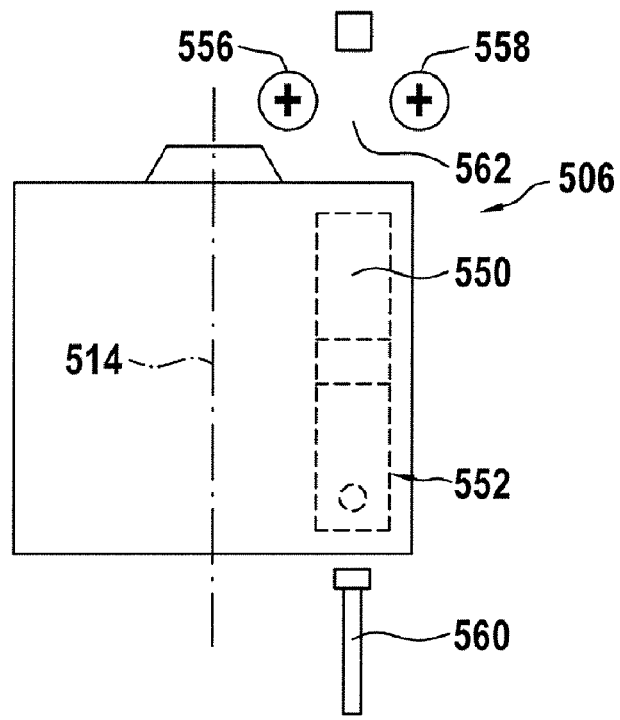
FIGS. 10 and 11 are schematic views of drum magazines with stored and pushed-out medical commodities.
Figure 11:
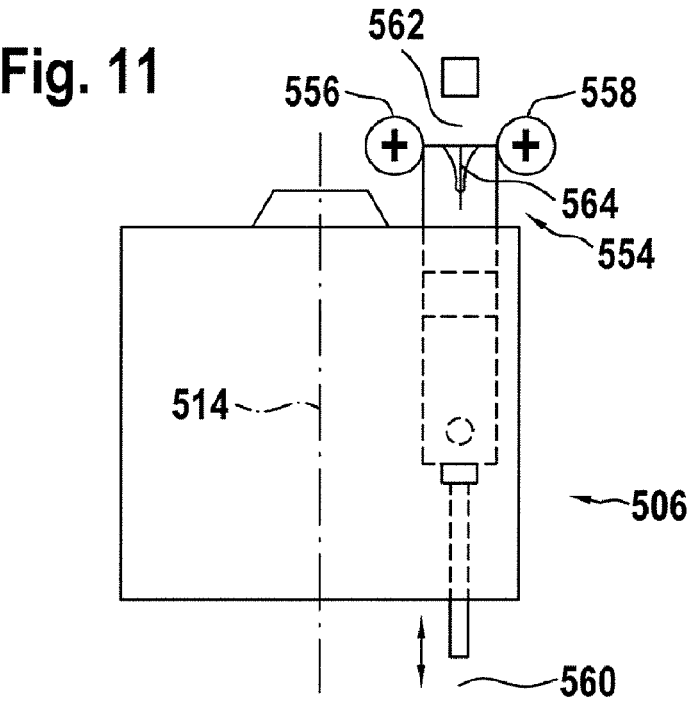

Drum magazines with stored and pushed-out medical commodities may be gathered from the illustrations of FIGS. 10 and 11.

A drum magazine 506 which is rotatable about its axis of rotation 514 is shown in schematically FIG. 10. The drum magazine 506 according to the illustration in FIG. 10 contains a plurality of medical commodities-illustrated in their storage position 552. These may take the form of, e.g., test strips having a sample application surface 564. The commodities 550 are moved by means of a plunger 560 from their storage position 552 illustrated in FIG. 10 into the extraction position 554 illustrated in FIG. 11. According to the illustration in FIGS. 10 and 11, it may be gathered that the drum magazine 506 is assigned in each case a conveying roller 556 and a counterroller 558, between which a transport gap designated by reference symbol 562 prevails. As soon as the plunger 560 is activated, the respective medical commodity 550 is pushed out of its storage position 552 in the drum magazine 506 into the gap 562.

It may be gathered from FIG. 11 that the medical commodity 550 illustrated here in test strip form is pushed into the transport gap 562 between the conveying roller 556 and the counterroller 558. The driven conveying roller 556 grasps the medical commodity 550, illustrated here in strip form, and conveys it into its extraction position 554, as illustrated in FIG. 11. The drum magazines 506 illustrated in FIGS. 10 and 11 may be integrated into an integrated system according to the illustration in FIG. 9.

Figure 12:
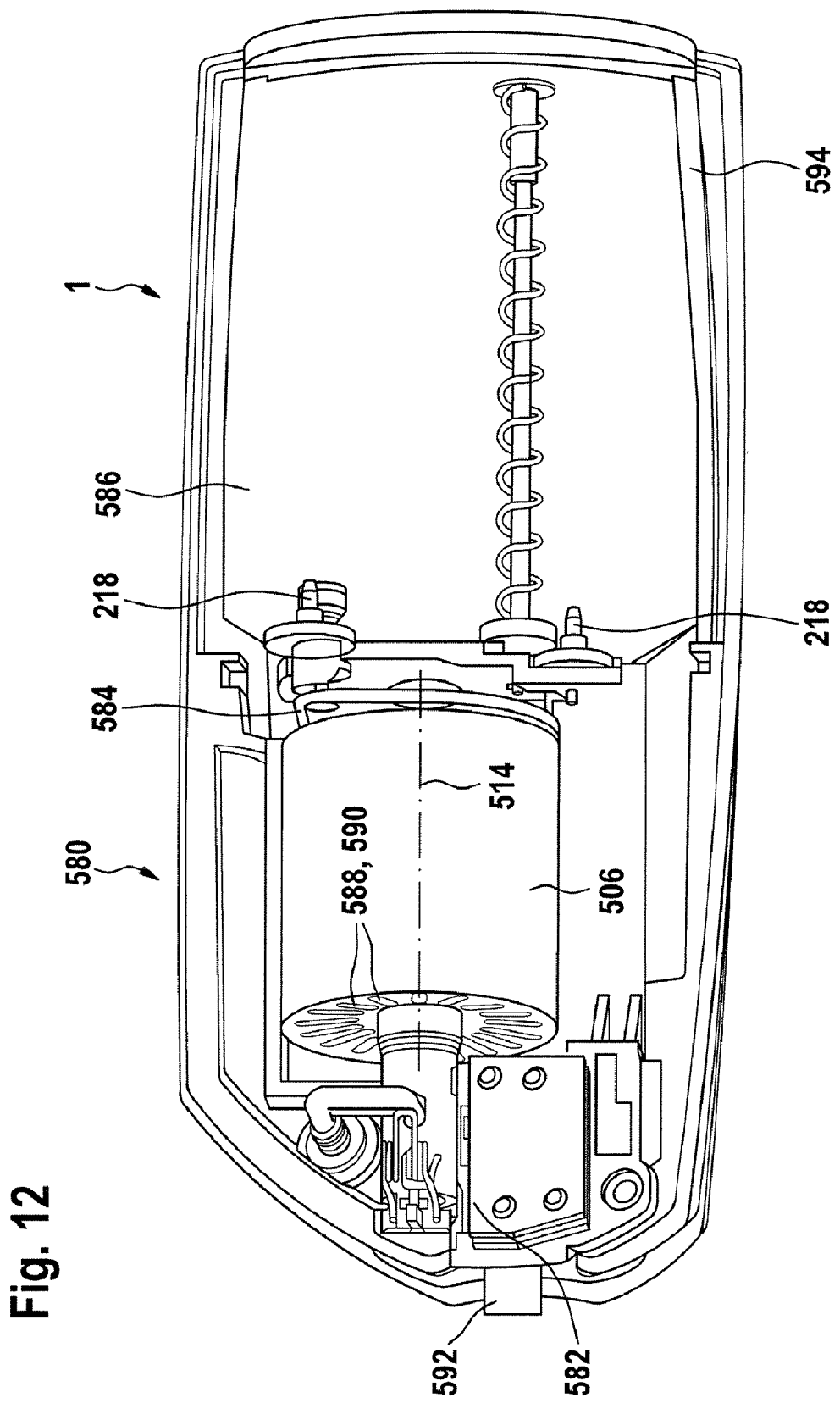
FIG. 12 is perspective view of a drum magazine received in an analyzer with the interior portion shown for viewing.

FIG. 12 shows a drum magazine received in an analyzer. It may be gathered from the illustration according to FIG. 12 that the analyzer 580 comprises a positioning device 582, by means of which the individual medical commodities 592—here in the form of test strips—received in the drum magazine 506 are positioned before being used by the user. The drum magazine 506 is driven by a drive unit 584. The drive unit 584 may itself be driven via an output shaft 218 of one of the drive units according to the above-described embodiments in FIG. 1, FIG. 3, FIG. 4 and according to FIGS. 5-7. When the drive unit is received in the analyzer 580, an installation space 586 is provided in the latter, which provides room for accommodating the drive unit. The analyzer 580 has a frame 594 for stiffening. For the sake of completeness, it may be mentioned that the drum magazine 506 has a multiplicity of reception chambers 588 which on one of their end faces contain in each case an extraction orifice 590 via which the test strips 592 can be delivered to the positioning device 582. The drum magazine 506 which is driven by the drive unit is moved about its axis of rotation 514.

Figure 13:
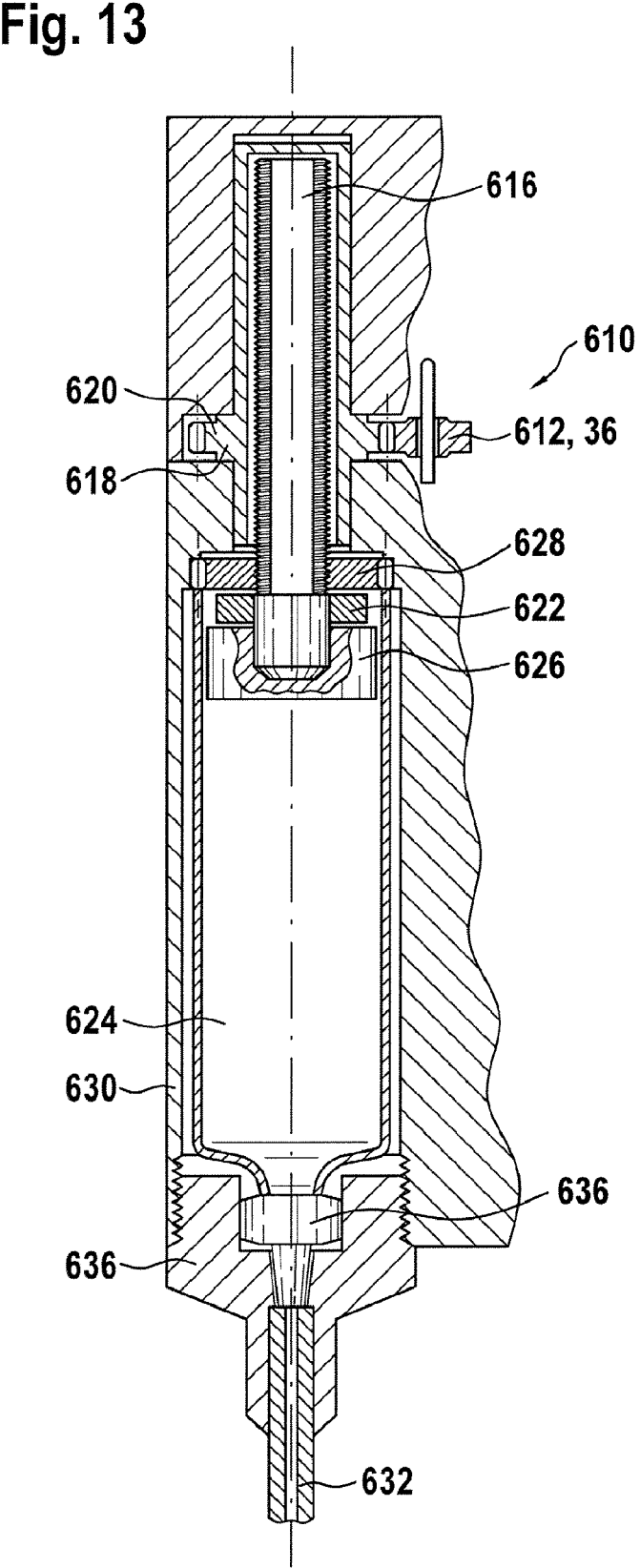
FIG. 13 is a cross sectional view of an insulin pump designed as a syringe.

An insulin pump designed as a syringe may be gathered from the illustration according to FIG. 13. The insulin pump 610 illustrated in FIG. 13 comprises a housing 630. A drive sleeve 618 which has an external teeth 620 is introduced into the housing 630. The external teeth 620 has meshing with it a driving wheel 612 which may be received, e.g., on the output shaft 218 of the piezoactuator 200, illustrated in FIG. 5, of an axial form of construction. By the drive unit being combined with a medical device, e.g., an insulin pump 610, a particularly long feed of a piston 626 is achieved which conveys the active substance—insulin in the present case—received in an ampoule 624 in the smallest possible quantities, but continuously, into a hose 632 which is connected to a catheter received in the human body. The insulin pump 610 according to the illustration in FIG. 13 comprises a threaded rod, the thread of which meshes with the internal teeth of a disk 628 having an external thread. Due to the external thread, the disk 628 is mounted fixedly in terms of rotation in the housing 630. When the threaded rod 616 is rotated continuously by means of the disk 628, the piston 626 moves continuously with the smallest possible feed into the ampoule 624. The ampoule 624 is locked in the housing 630 by means of a connection piece 636 and a cap 634 integrated into the latter.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SYMBOLS

- 10 Piezoactuator
- 12 Length change
- 14 Restoring element
- 16 Actuator head
- 18 Step-up element (lever-shaped)
- 20 First end
- 22 Second end
- 24 Axis of rotation
- 26 Direction of rotation step-up element
- 28 Bearing step-up element
- 30 First lever arm
- 32 Second lever arm
- 34 Nonreturn means
- 36 Ratchet wheel
- 38 Direction of rotation ratchet wheel
- 40 Secondary mechanical energy storage element
- 42 Detent pawl
- 44 Restoring element for detent pawl
- 46 Rotary bearing detent pawl
- 48 Direction of rotation detent pawl
- 50 Teeth
- 52 Hook
- 80 Clamping body freewheel
- 82 Clamping roller
- 84 Spring
- 86 Recess
- 88 Slope
- 90 Tubular surface
- 92 Shaft
- 100 Clamping roller freewheel with inner star
- 102 Inner star
- 104 Tubular body
- 106 Clamping body
- 108 Recess
- 110 Shaft
- 112 Double cage
- 114 Expanding band spring
- 116 Driver
- 120 Wrap spring coupling
- 122 Drive side
- 124 Output side
- 126 Spring
- 130 Frictional locking mechanism
- 132 Comb-shaped clamping ring
- 134 Shaft
- 136 Roller
- 138 Raised projections
- 140 Drive side
- 142 Output side
- 144 Clamping body ring
- 150 Piezoactuator with linear operation
- 152 Nonreturn means
- 154 Traveler
- 156 Guide
- 158 First traveler side
- 160 Second traveler side
- 170 Pricking drive (360° drive)
- 172 Pressure piece
- 174 Pivot bearing for lever
- 176 Abutment
- 178 Pivoting range first lever arm
- 180 Pedestal
- 181 Pressure piece with spherical head
- 182 Cam
- 183 Spring
- 184 Rotatable shaft
- 185 Axis of symmetry
- 186 Shaft bearing
- 188 First clamping roller freewheel
- 190 Second clamping roller freewheel
- 192 Outer ring first clamping roller freewheel
- 194 Device housing
- 200 Piezoactuator of axial form of construction
- 202 Lever pincer
- 204 Solid joint
- 206 First pincer leg
- 208 Second pincer leg
- 210 Drive bell
- 212 Torsion spring
- 214 Freewheel bell
- 216 Inner circumferential surface
- 218 Output shaft
- 220 Freewheel system
- 222 First short leg
- 224 Second short leg
- 226 First cam
- 228 Second cam
- 230 First extension (206)
- 232 Second extension (208)
- 234 Anti-twist device
- 236 Recess
- 300 Actuator with diaphragm
- 302 Cavity
- 304 Diaphragm thickness
- 306 Deflection
- 308 Wall of the cavity 302
- 310 Pressure medium
- 312 Direction of action on diaphragm
- 400 Actuator with micromotor
- 402 Output shaft
- 404 Direction of rotation
- 406 Contact surface
- 408 Cam
- 410 Electrical connection
- 412 90° rotation 414 Contact points cam 408
416 Oval contour
500 Combination drive unit
502 Secondary mechanical energy storage element
504 Gearwheel
506 Drum magazine
508 Shaft
510 Direction of rotation
512 Direction of rotation gearwheel
514 Axis of rotation drum magazine
530 Integrated system with pricking aid and magazine transport
532 Pricking aid
534 Shaft
536 Toothed structure (driver drum magazine)
538 Spiral spring
550 Medical commodity
552 Storage position commodity
554 Extraction position commodity
556 Conveying roller
558 Counterroller
560 Plunger
562 Gap
564 Sample application surface
580 Analyzer
582 Positioning device
584 Drum drive
586 Installation space for piezoactuator
588 Reception chambers
590 Extraction orifice
592 Test strip
594 Frame
610 Insulin pump
612 Driving wheel
614 Output shaft (as 218)
616 Threaded rod
618 Drive sleeve
620 External teeth
622 Disk
624 Ampoule
626 Piston
628 Disk with external thread
630 Housing
632 Hose
634 Cap
636 Outlet piece

What is claimed is:

1. A drive unit for a medical device, comprising:
a mechanical energy store;
an actuator which oscillates;
a nonreturn rotor or traveler for prestressing the mechanical energy store; and
a step-up element configured to transmit travel strokes of the actuator to the nonreturn rotor or traveler.

2. The drive unit of claim 1 further comprising an output shaft operably connected to the mechanical energy store.

3. The drive unit of claim 1 further comprising a plunger configured for pushing a medical commodity from a magazine, the plunger being operably connected to the mechanical energy store.

4. The drive unit of claim 1 further comprising a pump which administers a medically active substance, the pump being operably connected to the mechanical energy store.

5. The drive unit of claim 1, wherein the step-up element amplifies the stroke of the actuator in a ratio of at least 1:25 and transmits the amplified stroke to the nonreturn rotor or traveler.

6. The drive unit of claim 5, wherein the step-up element further comprises a restoring spring.

7. The drive unit of claim 6, wherein the nonreturn rotor comprises a ratchet wheel having teeth on its outer circumference.

8. The drive unit of claim 1, wherein the mechanical energy storage element comprises a spring element.

9. The drive unit of claim 1, wherein the step-up element comprises a first and a second lever arm having different lengths.

10. The drive unit of claim 9, wherein the actuator actuates one of the lever arms and the other of the lever arms actuates the nonreturn rotor or traveler.

11. The drive unit of claim 1, wherein the step-up element comprises a rocker in a device housing having a first and a second lever arm, the second lever arm configured to actuate a pivoting cam which rotates an output shaft.

12. The drive unit of claim 11, wherein the output shaft comprises a first clamping roller freewheel coupled to the pivoting cam and a second clamping roller freewheel coupled to the device housing.

13. The drive unit of claim 11, wherein the step-up element further comprises a spring-loaded pressure piece having a spherical head.

14. The drive unit of claim 1, further comprising a nonreturn element which counteracts a backward movement of the nonreturn rotor when the stroke movement of the actuator is reversed.

15. The drive unit of claim 14, wherein the nonreturn rotor comprises a ratchet wheel or a linear traveler having teeth.

16. The drive unit of claim 15, wherein the nonreturn element comprises a pawl configured to engage teeth of the ratchet wheel or the linear traveler.

17. The drive unit of claim 14, wherein the nonreturn element comprises a clamping body freewheel.

18. The drive unit of claim 1, wherein the nonreturn rotor or traveler comprises a nonreturn traveler having a first traveler side, a second traveler side, and a linear guide, the linear guide configured to receive the nonreturn traveler.

19. The drive unit of claim 18, wherein one of the two traveler sides comprises a comb-shaped rib structure that prevents a return movement of the nonreturn traveler.

20. The drive unit of claim 1, further comprising a lever pincer which is actuated by the actuator, the lever pincer having first and second pincer legs articulated by a joint.

21. The drive unit of claim 20, wherein the pincer legs comprise extension surfaces having drive cams that actuate a drive bell.

22. The drive unit of claim 21, wherein the drive bell surrounds a freewheel.

23. The drive unit of claim 22, wherein the freewheel is rotationally fixed on an output shaft.

24. The drive unit of claim 1, wherein the actuator comprises a piezoactuator, the stroke travel of the actuator being transmitted to the step-up element when a voltage is applied to the piezoactuator.

25. The drive unit of claim 1, wherein the actuator comprises a diaphragm configured to deflect when a cavity thereof is acted upon by pressure, thereby generating the travel strokes.

26. The drive unit of claim 1, wherein the actuator comprises a micromotor having an output shaft coupled to a cam that deflects the step-up element.

27. The drive unit of claim 26, wherein the cam is configured to deflect the step-up element at least once during a full rotation of the output shaft.

28. A drive unit for a medical device, comprising:
a mechanical energy storage element;
an actuator; and
a transmission element;
wherein the actuator produces oscillating travel strokes which oscillate the transmission element, the oscillations of the transmission element being at least partially transferred to the mechanical energy storage element as stored mechanical energy.

29. The drive unit of claim 28, further comprising a rotor or traveler configured to be advanced by the transmission element, the rotor or traveler thereby charging the mechanical energy storage element.

30. The drive unit of claim 29, further comprising a nonreturn element which prevents the rotor or traveler from moving in a reverse direction.

31. The drive unit of claim 30, wherein the nonreturn element comprises a ratchet.

32. The drive unit of claim 28, wherein the transmission element comprises a pivotable lever that is engageable by the actuator.

33. The drive unit of claim 32, further comprising a rotor or traveler disposed between the pivotable lever and the mechanical energy storage element, the pivotable lever advancing the rotor or traveler as the pivotable lever oscillates.

34. The drive unit of claim 33, wherein the pivotable lever comprises first and second level arms, the first lever arm being engaged by the actuator and the second level arm engaging the rotor or traveler, the second lever arm being longer than the first lever arm, whereby the pivotable lever amplifies the travel strokes from the actuator.

35. The drive unit of claim 28, wherein the mechanical energy storage element comprises a spring.

36. The drive unit of claim 28, further comprising a movement element that is driven by the mechanical energy storage element.

37. The drive unit of claim 36, wherein the movement element comprises an output shaft.

38. The drive unit of claim 36, wherein the movement element comprises a plunger configured for pushing a medical consumable from a magazine.

39. The drive unit of claim 36, wherein the movement element comprises a pump for pumping a medically active substance.

40. A drive unit for a medical device, comprising:
an actuator;
a mechanical energy storage element;
a rotor or traveler operably connected to the mechanical energy storage element;
a nonreturn element that prevents a reverse movement of the rotor or traveler; and
a pivotable lever disposed between the actuator and the rotor or traveler, the pivotable lever being configured to transmit movement of the actuator into an advancing movement of the rotor or traveler which thereby charges the mechanical energy storage element.

41. The drive unit of claim 40, wherein the actuator oscillates the pivotable lever.

42. The drive unit of claim 41, wherein the pivotable lever comprises a first lever arm that is engageable by the actuator and a second lever arm that engages the rotor or traveler.

43. The drive unit of claim 42, wherein the second lever arm is longer than the first lever arm, whereby the pivotable lever amplifies the oscillations.

44. The drive unit of claim 40, wherein the nonreturn element comprises a ratchet.

45. The drive unit of claim 40, wherein the mechanical energy storage element comprises a spring.

46. The drive unit of claim 40, further comprising a movement element that is driven by the mechanical energy storage element.

47. The drive unit of claim 46, wherein the movement element comprises an output shaft.

48. The drive unit of claim 46, wherein the movement element comprises a plunger configured for pushing a medical consumable from a magazine.

49. The drive unit of claim 46, wherein the movement element comprises a pump for pumping a medically active substance.

50. A method of actuating a drive unit in a medical device, comprising:
oscillating a step-up element with an actuator;
converting the oscillation of the step-up element into an advancing movement of a rotor or traveler while preventing reverse movement of the rotor or traveler;
converting at least a portion of the advancing movement of the rotor or traveler into energy stored by a mechanical energy storage element; and
releasing the energy in the mechanical energy storage element to actuate the medical device.

51. The method of claim 50, wherein the medical device comprises a lancet system and the releasing of the energy in the mechanical energy storage element comprises driving a lancet of the lancet system in a puncturing direction.

52. The method of claim 50, wherein the releasing of the energy in the mechanical energy storage element comprises transporting medical consumables.

53. The method of claim 50, wherein the releasing of the energy in the mechanical energy storage element comprises driving a pump to convey a medical substance from a container.

54. The method of claim 50, wherein the releasing of the energy in the mechanical energy storage element comprises driving an insulin pump for conveying insulin from an exchangeable ampoule.

55. The method of claim 50, wherein the mechanical energy storage element comprises a spring and the step of releasing the energy in the mechanical energy storage element comprises discharging the spring.

56. The method of claim 55, wherein the medical device comprises a lancet system and the discharging of the spring comprises driving a lancet of the lancet system in a puncturing direction.

* * * * *

UNITED STATES PATENT AND TRADEMARK OFFICE
CERTIFICATE OF CORRECTION

PATENT NO.       : 7,456,550 B2
APPLICATION NO.  : 11/832458
DATED            : November 25, 2008
INVENTOR(S)      : Frank Deck Page 1 of 1

It is certified that error appears in the above-identified patent and that said Letters Patent is hereby corrected as shown below:

In column 4, line 3, please change "clement" to -- element --.

Signed and Sealed this

Seventeenth Day of March, 2009

JOHN DOLL
*Acting Director of the United States Patent and Trademark Office*